United States Patent [19]

Rei

[11] Patent Number: 4,686,239

[45] Date of Patent: Aug. 11, 1987

[54] SOLID BIOCIDE DRY BLEND

[75] Inventor: Nuno M. Rei, Boxford, Mass.

[73] Assignee: Morton Thiokol, Inc., Chicago, Ill.

[21] Appl. No.: 937,810

[22] Filed: Dec. 4, 1986

Related U.S. Application Data

[60] Division of Ser. No. 853,083, Apr. 17, 1986, Pat. No. 4,663,359, which is a continuation-in-part of Ser. No. 707,628, Mar. 4, 1985, abandoned.

[51] Int. Cl.$^4$ ............................................. C08J 9/00
[52] U.S. Cl. ........................................ 521/55; 521/57; 521/89; 521/90; 521/93
[58] Field of Search ...................... 521/55, 57, 89, 90, 521/93

[56] References Cited

U.S. PATENT DOCUMENTS

| | | | |
|---|---|---|---|
| 3,371,053 | 2/1968 | Raskin | 521/56 |
| 3,644,238 | 2/1972 | Smith | 521/55 |
| 4,229,547 | 10/1980 | Cohen et al. | 521/69 |
| 4,360,651 | 11/1982 | Dinbergs | 526/88 |
| 4,391,920 | 7/1983 | Lange | 521/61 |
| 4,435,524 | 3/1984 | Dinbergs | 521/65 |
| 4,454,198 | 6/1984 | Fickel et al. | 428/402 |
| 4,458,057 | 7/1984 | Basu | 526/88 |
| 4,464,519 | 8/1984 | Mango | 526/200 |

Primary Examiner—Morton Foelak
Attorney, Agent, or Firm—Richard J. Sheridan; Gerald K. White

[57] ABSTRACT

A composition comprising a dry blend mixture of a porous thermoplastic resin powder and from 1 to 80 wt. % of a microbiocide based upon the weight of the composition. The microbiocide is present in the mixture at a concentration of at least about 20 times greater than the normal upper usage concentration of the microbiocide, and is held within the pores of the thermoplastic powder.

The resulting concentrate is a substantially non-dusting, free-flowing powder which is readily incorporated into a second thermoplastic resin to produce a resulting article having the appropriate level of microbiocide.

4 Claims, No Drawings

SOLID BIOCIDE DRY BLEND

This is a divisional of co-pending application Ser. No. 853,083 filed on Apr. 17, 1986, now U.S. Pat. No. 4,663,359 which is in turn a continuation-in-part of Ser. No. 707,628 filed on Mar. 4, 1985, now abandoned.

BACKGROUND OF THE INVENTION

The present invention relates to solid biocide dry blend concentrates and methods of making such concentrates.

Resin compositions are protected against fungal or bacterial attack by incorporating a microbiocide therein to prevent the deterioration of articles formed from the resin composition due to microbiological attack on the susceptible portion of the components of the resin system. In order for the microbiocide to be effective in the resin composition, it is necessary that it be compatible therewith and uniformly dispersible in the resin composition to avoid forming resin composition portions free of the microbiocide which would be susceptible to attack.

In the past, microbiocide compositions have been added to resins either as a powder or as a liquid composition. To assure compatibility and adequate dispersibility of the microbiocide, it was believed necessary to add the microbiocide with a liquid carrier, such as a plasticizer for the resin. The presently employed procedures usually involve first mixing the microbiocide in a liquid carrier which solubilizes or disperses the microbiocide uniformly, followed by mixing the liquid composition with the final resin composition. The liquid solvents or dispersants employed are those such as plasticizers which do not degrade the properties of the final resin product when employed at moderate concentrations. Unfortunately, the solubility of many of the commonly used microbiocides in common liquid resin additives is quite low. Therefore, it is difficult to incorporate a sufficiently high concentration of the microbiocide with the resin while avoiding an undesirably high concentration of the liquid carrier. Also, this procedure imposes restrictions on the choice of plasticizer to be used in the final resin composition. In addition, it is desirable to avoid using plasticizers with some thermoplastic resins such as polyurethanes and polyolefins.

Alternatively, it has been proposed to add the microbiocide directly to a formable resin composition at the low effective concentration which prevents microbiological attack. However, this procedure has proven to be unsatisfactory since the needed concentration of microbiocide is quite low, generally less than about one wt. % and usually between about 200 and 1000 parts per million. If the microbiocide were to be employed in the resin at higher concentration, the toxicity of the final product made therefrom may be dangerously increased. Therefore, if this procedure is employed, the processor must continously carefully weigh small amounts of microbiocides to be added to the final product. Since most microbiocides available for protecting resins are powders, continuous handling of a fine-powdered solid which can easily be dispersed in air presents a major toxicological problem to the personnel working in the immediate area. To eliminate these toxicological problems, major changes would be required in presently employed commercial plastic processing techniques which would render them expensive and commercially unfeasible. For this reason, the commercial processor utilizes the microbiocide in a liquid carrier which is somewhat less innocuous than the microbiocide per se. In addition, in order to attain homogeneous dispersion of these low concentrations of microbiocide into the resin, it is necessary to extend the mixing time of the resultant composition. Furthermore, mixing of these resin compositions containing low concentrations of microbiocides results in a substantial portion of the microbiocide being coated on the surface of the mixing apparatus rather than being homogeneously dispersed throughout the resin.

One solution to many of these problems is described in U.S. Pat No. 4,086,297. The U.S. Pat. No. 4,086,297 describes a solid microbiocide concentrate composition comprising a homogeneous mixture of a solid thermoplastic resin and from 1 to 80 wt. % of at least one microbiocide which is insoluble in water. The microbiocide is readily dispersible or soluble in the resin at temperatures sufficiently high to permit plastic manipulation of the resin and the dispersion or solution of the microbiocide is sustained indefinitely upon cooling to ambient temperature while the diffusivity of the microbiocide in the resin under such conditions becomes vanishingly small. The microbiocide retains its microbiocidal activity in the resin and does not degrade or react with the resin in which it is dispersed. The composition described therein provides a convenient non-toxic dosage form of the microbiocide which is subsequently mixed with a second thermoplastic resin at a concentration of about 0.5 to 15 wt. % to obtain a homogeneous resin composition containing an effective amount of the microbiocide.

Although the U.S. Pat. No. 4,086,297 describes compositions acceptable in most instances, certain disadvantages remain. The process used to prepare the compositions of the U.S. Pat. No. 4,086,297 includes heating the microbiocide and resin to melt and soften the resin and to form a homogeneous mixture. The homogeneous mixture is subjected to shear forces and heat in a suitable apparatus and then formed, such as by extrusion, milling or calendering. After cooling, the formed composition is broken up into small particles, e.g., pellets, thereby permitting its incorporation into other thermoplastic compositions to provide an appropriate concentration of microbiocide.

The particles resulting from the above process are not suitable for incorporation into plastisols. Nor are such particles usable when screening to filter out impurities such as paper, etc. is performed in preparing a dry blend prior to extrusion. In addition, the heating, mixing and cooling steps of the process of the U.S. Pat. No. 4,086,297 are relatively high in terms of energy costs. Finally, the heating step of the process of the U.S. Pat. No. 4,086,297 means that microbiocides which are heat sensitive cannot be used therein.

Another attempt at solving the problem of handling dusty additives which may be toxic is set forth in U.S. Pat. No. 4,025,690. The U.S. Pat. No. 4,025,690 describes a process for preparing pigment additives for plastic materials in which the dusty additives are absorbed by a polymer or copolymer of vinyl chloride in granular form. The process consists of treating the additives and polymer or copolymer in a mixer while raising the temperature to obtain absorption of the additive by the particles of the polymer or copolymer. The mass is then cooled to ambient temperature. While appropriate for some additives, powdery additives, such as microbiocides, continue to be dusty even after absorption, and much of the biocide remains on the surface of the resin where it can flake off and cause excessive dusting during handling. The biocide can be readily seen on the surface of the resin particles by microscopic examination.

Accordingly, a need exists for a microbiocide concentrate which is useful in plastisol formulations, is more simply prepared than prior art concentrates, and allows a broader range of microbiocides to be employed, while retaining the reduced toxicity and ease of handling of the compositions of the U.S. Pat. No. 4,086,297.

SUMMARY OF THE INVENTION

The present invention is a composition comprising a dry blend mixture of a non-foamed, non-cellular porous thermoplastic resin powder and from 1 to 80 wt. % of a microbiocide based upon the weight of the composition. The microbiocide is present in the mixture at a concentration of at least about 20 times greater than the normal upper usage concentration of the microbiocide, and is held within the pores of the thermoplastic powder.

The resulting concentrate is a substantially non-dusting, free-flowing powder which is readily incorporated into a second thermoplastic resin to produce a resulting article having the appropriate level of microbiocide.

DETAILED DESCRIPTION OF THE INVENTION

The compositions of this invention contain the microbiocide at a concentration which permits the subsequent incorporation of the resultant composition into a second thermoplastic resin composition at a concentration between about 0.5 and 15 wt. % based upon the total weight of the resultant composition. When less than about 0.5 wt. % of the composition of this invention is incorporated into the second thermoplastic resin composition, less than homogeneous dispersion may be obtained which causes the resultant composition to have under-protected areas. When more than about 15 wt. % of the compositions of this invention is incorporated into a second thermoplastic resin which is different than the first thermoplastic resin, the two resins may become incompatible. In addition, when more than about 15 wt. % of the composition of this invention is incorporated into a second thermoplastic resin, undesirable changes in the physical characteristics of the second thermoplastic resin occur in that they approach those of the first thermoplastic resin.

The concentration of microbiocide in the composition of this invention is between about 1 and 80 wt. %, preferably from about 5 to about 55 wt. %, based upon the total weight of the thermoplastic composition. The microbiocide concentration depends upon the particular microbiocide and composition and its relative compatibility in the resin. In each instance, the microbiocide concentration is at least about 20 times greater than its normal upper usage concentration in the final resin composition. For example, 10,10'-oxybisphenoxarsine is used normally in a concentration up to 0.05 wt. %; N-(trichloromethylthio)-4-cyclo-hexene-1,2-dicarboximide is used normally in a concentration up to 0.5 wt. %; 2,3,4,6-tetrachloro-4methylsulfonyl)pyridine is used normally in a concentration up to 0.75 wt. %; and N-(trichloromethylthio)-phthalamide is used normally in a concentration up to 0.2 wt. %. In any event, the microbiocide concentration is controlled so it is present in an effective concentration in a second thermoplastic resin composition when added thereto at between about 0.5 and 15 wt. % based upon the weight of the second thermoplastic resin composition.

In order to form the compositions of the present invention, the microbiocide must be a liquid at the temperature at which the pores of the porous resin open, or be readily soluble in a carrier which is readily absorbable by the porous resin. In addition, the microbiocide must be substantially retained within the porous resin powder until such time as the microbiocide containing powder is processed into the final article. The microbiocide must also retain its activity and not itself become degraded or degrade the resin either during mixing to produce the dry blend or after being incorporated into the resin. Stability of the microbiocide-resin concentrate is determined readily by visual observation wherein irreversible discoloration of the concentrate represents degradation of the composition so that it is not useful in the present invention. For example, the microbiocide, ortho-benzyl parachlorophenol is miscible in resins, particularly vinyl resins but the resultant resin-microbiocide composition turns irreversibly black and therefore is not useful herein.

The degree of retention of microbiocidal activity in the resin-microbiocide concentrate is determined in any conventional manner wherein the concentrate is incorporated into a plasticized second resin to obtain a composition containing the normal upper range concentration of the microbiocide. This composition then is placed in a petri dish, innoculated with a microorganism against which the microbiocide is normally effective and the zone of inhibition is observed in a conventional manner.

Since the microbiocide in the concentrate is retained within the resin, the potential for human exposure is reduced relative to the microbiocide per se or the microbiocide in solution, even though present at higher concentrations than its effective concentration as a microbiocide. Accordingly, it can be incorporated subsequently in a second thermoplastic resin composition with reduced hazard to working personnel since the dusting problem associated with the powdered microbiocides is eliminated. Furthermore, the composition of this invention reduces contamination of processing and weighing equipment and facilitates clean-up of this equipment.

The compositions of this invention are not meant to have useful end use mechanical properties. Therefore, they must be incorporated into another thermoplastic resin to produce useful fabricated thermoplastic products. However, due to their less toxic nature, the composition of this invention provides a significant advantage over the prior art compositions which do not use concentrates in that they can be processed safely by conventional thermoplastic resin fabrication techniques without requiring costly safety equipment and without the need for a liquid carrier for the microbiocide. Moreover, as compared to pellets, the dry blended powders of the present invention are easier to disperse, do not get caught in screens, and can be measured out more accurately.

The compositions of the present invention are prepared by mixing a porous thermoplastic resin powder with a high concentration of microbiocide. A high intensity-high shear mixer is used to perform the mixing, e.g. a Henschel mixer. Any of those mixers well known in the art may be used including, for example, a centrifugal impact mixer, high speed dispersion mixer, ribbon blender, conical dry blender, double arm mixer, vortical action mixer, and other such mixers, such as those described in "The Encyclopedia of Plastic Equipments" by Herbert R. Simons, Reinhold Pub. Corp., New York, N.Y. (1964).

When the powder and microbiocide are initially combined, very little absorption occurs. As mixing is performed, the mixture continues to heat up due to an external heat source and/or friction and collisions between the particles until the pores of the resin open and absorb the microbiocide. At this temperature, commonly referred to as the "drop temperature", the liquid has been completely absorbed by the resin and the mixture is cooled down to obtain a dry, free-flowing powder containing the microbiocide. The drop temperature will vary depending on the resin, the microbiocide, whether a carrier has been employed to dissolve the microbiocide, and the concentration of microbiocide. The drop temperature will typically vary between about 160° F. and 220° F.

The porosity of the porous resin is particularly important in the practice of the present invention. Various resins are known in the art which would be suitable for use in the present examples. The porosity should typically be between about 30–70% when measured on a void volume basis, or about 0.10–0.60 cc/g when measured by the mercury intrusion method (ASTM D2873). Using this latter method, the measurement is made by forcing mercury under pressure into the pores of the resin. The volume of mercury forced into the resin is measured and recorded as cc/g. The particle size of the powder is typically between about 40 and about 300 mesh. Typical porous resins powders for use in the present invention include those disclosed in U.S. Pat. No. 4,229,547 to Cohen et al. (issued Oct. 21, 1980); 4,360,651 to Dinbergs (issued Nov. 23, 1982); 4,391,920 to Lange (issued July 5, 1983); 4,435,524 to Dinbergs (issued Mar. 6, 1984); 4,454,198 to Fickel et al. (issued June 12, 1984); 4,458,057 to Baser (issued July 3, 1984) and 4,464,519 to Mango (issued Aug. 7, 1984). Each of these patents is hereby incorporated by reference herein. These patents describe various porous thermoplastic resin powders and how they are made. The porous thermoplastic resin powders useful in this invention have tiny interstices or "channels" within each resin particle which accounts for their high porosity. They are not, however, foams or cellular in nature. Examples of these porous thermoplastic resin powders include porous polyvinyl chloride resins available from B. F. Goodrich Chemical Co. under the trademark "GEON" and from General Tire & Rubber Co. under the trademark "VYGEN"; porous polyethylene, polypropylene and nylon resins available from Armak under the trademark "ACCUREL"; porous styrene-butadiene, polycarbonate, polyolefin, polystyrene, polyphenylene oxide, polystyrene-polyphenylene oxide blends; and ethylene/acrylic acid salts (ionomers). However, any such suitable porous resin powder having the appropriate porosity may be used in the practice of the present invention.

Suitable microbiocides include:
OBPA—10,10′-oxybisphenoxarsine
Vancide 89—N-(trichloromethylthio)-4-cyclohexene-1,2-dicarboximide
Dowcil A-40—2,3,5-trichloro-4-propylsulfonyl pyridine
Zinc Omadine—zinc salt of 1-hydroxypyridine-2-thione
Fungitrol 11—N-(trichloromethylthio) phthalimide
N-(2-methylnaphthyl) maleimide
Difolatan—cis-N-(1,1,2,2-tetrachloroethyl)-thio-4-cyclohexene-1,2-dicarboximide
Isolan—1-isopropyl-3-methyl pyrazolyl-5-dimethyl carbamate
3-methyl-pyrazolyl dimethylcarbamate
Maneb—manganese ethylene bisdithiocarbamate
Zineb—zinc analog of Maneb
Nabam—disodium analog of Maneb
Ferbam—ferric dimethyl dithiocarbamate
Ziram—zinc analog of Ferbam
Karathane—2,4-dinitro-6-capryl phenol crotonate
Ovotran—p-chlorophenyl-p-chlorobenzenesulphonate
Skane M-8—2-N-octyl-4-isothiazolin-3-one
Benomyl—methyl-1(butylcarbamoyl)-2-benzimidazole carbamate
Metasol TK-100—2-(4-thiazolyl) benzimidazole
Copper-8—copper 8-hydroxy-quinolinate
α-diethoxyphosphinodithioacetylurea
α-dimethoxyphosphinodithioacetylurea
Diethoxyphosphinodithioacetamide
Dimethoxyphosphinodithioacetamide
Bis(dimethylamido) phosphoryl fluoride
Tributyl tin fluoride
2-cyclohexyl-3-isothiazolone
4,5-dichloro-2-cyclohexyl-3-isothiazolone and mixtures thereof.

The preferred microbiocides are 10,10′-oxybisphenoxarisine; N-(trichloromethylthio)-4-cyclohexene-1,2-dicarboximide; 2,3,5,6-tetrachloro-4-(methylsulfonyl) pyridine; N-(2-methylnaphthyl) maleimide; and N-(trichloromethylthio) phthalimide since they are relatively easy to incorporate into a wide variety of resins at high concentration without significant loss of microbiological activity and without significant degradation of the resin.

If the microbiocide is a solid at ambient temperatures, it must be dissolved in a suitable carrier prior to mixing with the porous resin powder or melted during the mixing stage. The carrier must be inert to the microbiocide, the resin powder, the resin of the ultimate product, and any other ingredients of any of the above. Suitable carriers include commonly used plasticizers such as the phthalates, azelates, adipates, sebates, and epoxidized soybean oil. The carrier is used in amounts sufficient to dissolve the microbiocide, and preferably in the minimum amount necessary to do so since excess amounts may adversely affect the properties of the concentrate and the ultimate article.

A carrier substantially improves the transport of biocide into the resin particle matrix during the dry blending cycle. On cooling, the biocide is trapped in the resin particle. If a carrier is not used and the biocide does not melt during mixing, much of the biocide remains on the surface of the resin where it can flake off and cause excessive dusting during handling. Such unabsorbed biocide can be readily seen on the surface of the resin particles by microscopic examination.

The compositions of this invention are blended with a second thermoplastic composition by conventional means. The concentrated microbiocide-resin composition can be added during compounding of the second thermoplastic composition or can be incorporated therein after it has been compounded but prior to fabrication of the second thermoplastic composition in any conventional manner such as extrusion, melting or calendering. All that is required is that the microbiocide-containing composition and the second thermoplastic composition be compatible so that a homogenous final composition results. The microbiocide-containing composition should have a softening temperature below or within the range of temperatures encountered during conventional processing of the second thermoplastic composition. These temperatures are within the range of between about 250° F. and about 600° F. It is preferred that the resin-microbiocide concentrates have a softening temperature within the range of about 200° F. to 500° F.

In forming the microbiocide-containing composition of this invention, the usual resin additives optionally can be included. If desired, a plasticizer for the resin can be incorporated with the composition. However, it has been found that when higher concentrations of microbiocide are employed, a reduced concentration of plasticizer must be employed to avoid incompatibility of the microbiocide and resin. The concentration of plasticizer that can be tolerated in the compositions of this invention also is dependent upon the chemical compositions of the resin, the plasticizer and the microbiocide. Generally, moderate plasticizer concentrations can be tolerated within the range of between about 5 and 20 wt. % when the microbiocides are employed at concentrations of 50 wt. % or above. Higher plasticizer concentrations can be employed with lower concentrations of microbiocide. Thus, while the compositions of this invention can be made without plasticizers, it should be noted that it is not intended that this invention be limited by their exclusion.

To determine suitable plasticizers of a particular resin-microbiocide system, all that is necessary is the addition of the plasticizer, within the range noted above, to the resin-microbiocide composition, mixing of the resultant composition, and a visual determination for homogeneity. Any of the conventional resin plasticizers can be employed including dialkyl phthalates, epoxy plasticizers, polyester plasticizers, dialkyl phosphites and the like. In addition, the usual resin additives can be included such as ultraviolet stabilizers, heat stabilizers, fillers, dyes, pigments, lubricants and the like.

Representative suitable thermoplastic resins which can be compounded with the microbiocide-resin compositions of the present invention include polyvinyl chloride, vinyl chloride-vinyl acetate copolymers, polyurethanes, polyamides, polyolefins, polystyrene, vinyl chloride-acrylonitrile copolymers, polyesters and the like.

The concentrates of the present invention are more readily and less expensively made than the concentrates of the prior art. Moreover, the compositions of the present invention are more rapidly dispersed in the resin than the concentrates of the prior art. It is also possible to use a wider range of biocides since lower processing temperatures are involved in making the concentrate. Another advantage is more accurate measuring or metering.

In order to further illustrate the present invention and the advantages thereof, the following specific examples are given, it being understood that these examples are intended only to be illustrative without serving as a limitation on the scope of the present invention.

EXAMPLES 1 AND 2

These examples illustrate the production of a typical concentrate according to the present invention.

The following ingredients are mixed in a Henschel mixer at the wt. % indicated:

|  | Ex. 1 | Ex. 2 |
| --- | --- | --- |
| Porous polyvinyl chloride resin (Diamond 450 PVC) | 65.00 | 55.50 |
| Dioctyl phthalate plasticizer | 20.00 | 17.23 |
| N—(2-methylnaphthyl) maleimide | 12.50 | 25.00 |
| Ca, Zn stabilizer (Mark 538) | 0.50 | 0.50 |
| Epoxidized soybean oil plasticizer | 1.83 | 1.60 |
| Stearic acid | 0.17 | 0.17 |
| Total | 100.00 | 100.00 |

The average particle size of the resin is 40–140 mesh, and the average porosity is 0.21–0.30 cc/g (ASTM D2873).

The mixture is mixed until a drop temperature of 180° F. is obtained, at which time the microbiocide is absorbed resulting in a free-flowing non-dusting powder which is cooled.

EXAMPLES 3 AND 4

These examples illustrate that the dry blend concentrate of the present invention can be extruded and pelletized.

The dry blend of Example 1 is extruded at temperatures of 150° and 160° C. and at 125 rpm, and the dry blend of Example 2 is extruded at temperatures of 140° and 150° C. The dry blends are extruded alone or in combination with 0.1 wt. % of color tracer (Carmine Red HF-3C). After extrusion and cooling, the extruded rod is pelletized.

Each of the dry blends extrudes and pelletizes well. The pellets not containing color tracer are a clear yellow color, and the pellets containing the color tracer are a clear and uniform red color.

EXAMPLES 5 AND 6 AND COMPARATIVE EXAMPLES A AND B

The dispersion characteristics of the microbiocide-dry blend formulations of Examples 1 and 2 in a typical low plasticizer level base are compared by the gel-count method to the same base without added microbiocide-dry blend (Comparative Example A) and the same base to which is added the same amount of raw polyvinyl chloride resin (Comparative Example B).

The formulation of the base is as follows:

| Component | Weight (g) |
| --- | --- |
| Polyvinyl chloride resin | 100.00 |
| Di-2-ethylhexyl phthalate | 40.00 |
| Epoxidized soybean oil | 7.70 |
| UV Stabilizer (Mark 202A) | 1.00 |
| Heat Stabilizer (Mark KCB) | 3.50 |
| Heat Stabilizer (Mark C) | 1.50 |
| Stearic Acid | 0.25 |

Films are prepared by milling the components of the base until a uniform dispersion is obtained, at which time about 0.05% by weight of carbon black is added to each of the four samples and 1% by weight of the dry blend of Example 1 (Example 5), Example 2 (Example 6) or raw PVC resin (Comparative Example B) is added. Milling is continued for five additional minutes and then each sample is drawn out into a thin film approximately 2 to 3 mils in thickness.

The number of gels per square inch are counted with the following results:

| Example | Observation 1 | 2 | 3 | Average |
|---|---|---|---|---|
| 5 | 5 | 7 | 6 | 6.0 |
| 6 | 5 | 6 | 8 | 6.3 |
| A | 4 | 8 | 6 | 6.0 |
| B | 8 | 9 | 10 | 8.3 |

From these results, it can be seen that the dry blends of Examples 1 and 2 readily disperse in the base formulation, whereas the sample containing raw PVC (Comparative Example B) contains areas which are not homogeneous.

EXAMPLES 7 AND 8

The dry blends of Examples 1 and 2 can also be tested for dispersion by the color tracer method. Pellets of dry blend from Example 3 (Example 7) and Example 4 (Example 8), each containing color tracer, are blended with the following highly plasticized formulation:

| Component | Weight (g) |
|---|---|
| PVC Resin | 100 |
| Santicizer 711 | 32 |
| Diisodecyl phthalate | 40 |
| Epoxidized soybean oil | 6 |
| Mark KCB (Ba, Cd, Zn) | 3 |
| Mark 446 (U.V. stabilizer) | 0.5 |
| Thermolite 49 (Tin) | 1 |
| Calcium Stearate | 0.29 |
| Stearic Acid | 0.29 |
| TiO$_2$ | 29 |
| Atomite (calcium carbonate) | 10 |

The resulting blends are extruded at temperatures of 150° and 160° C. at 75 rpm using a ribbon die. There is no trace of uneven color distribution in either of the extruded ribbons indicating uniform dispersion of the dry blend and microbiocide throughout the ribbon.

EXAMPLE 9

The following example illustrates that stratification and separation do not occur in the dry blend during shipping and handling.

The following sample is prepared, the ingredients being present in the indicated wt. %:

| Ingredients | |
|---|---|
| Polyvinyl chloride resin (Diamond PVC 450) | 73.0 |
| N—(2-methylnaphthyl) maleimide | 12.5 |
| Calcium-zinc stabilizer | 0.5 |
| Diisodecyl phthalate | 14.0 |
| Total | 100.0 |

The sample is prepared by blending in a Henschel mixer to a drop temperature of 220° F., and then cooling.

A sample is placed in a container which is placed in the trunk of an automobile and removed after the automobile has traveled 1200 miles.

Representative portions from the top, middle and bottom of the container are analyzed for microbiocide [N-(2-methylnaphthyl maleimide] with the following results:

| wt. % | | |
|---|---|---|
| Top | Middle | Bottom |
| 13.4 | 14.1 | 13.4 |

From these results, it can be concluded that no significant migration or stratification of the microbiocide occurs during transportation and handling.

EXAMPLES 10 AND 11

The following examples illustrate the production of a typical concentrate according to the present invention using a different microbiocide than used in the preceding examples.

The following ingredients are mixed in a Henschel mixer at the wt. % indicated:

| | Ex. 11 | Ex. 12 |
|---|---|---|
| Porous polyvinyl chloride resin (Diamond 450 PVC) | 78.5 | — |
| Porous polyvinyl chloride resin (Pantasote XTR-3) | — | 79.5 |
| Diisodecyl phthalate (DIDP) plasticizer | 15.0 | 15.0 |
| 10,10'-oxybisphenoxarsine (OBPA) | 5.0 | 5.0 |
| Ca, Zn stabilizer (Mark 538) | 0.5 | 0.5 |
| Stearic acid | 1.0 | — |

In each example, the resin is heated in the Henschel mixer at 200° F., followed by the addition of a solution of the OBPA and DIDP which has been heated to 320° F. The temperature of the mixtures is then raised to 210° F. Next, the stabilizer and stearic acid are added. Mixing is continued until a drop temperature of 220° F. is obtained, at which time the microbiocide is absorbed, resulting in a free-flowing non-dusting powder which is cooled.

EXAMPLE 12 AND COMPARATIVE EXAMPLE C

The following examples illustrate the importance of the microbiocide either being a liquid at the drop temperature or being dissolved in a carrier prior to mixing with the porous resin.

Dry blends are prepared in a Henschel Mixer by blending all of the ingredients until the temperature reaches 220° F. The blend of Comparative Example C is prepared by an addition of biocide directly to the resin. The blend of Example 12 is prepared by first dissolving the biocide in dioctyl phthalate plasticizer by heating to 250° F. The hot solution is added directly to the resin during the mixing cycle. During preparation and during discharge from the Henschel Mixer, both blends are observed to determine whether dusting occurs. The biocide dry blend particles are also examined under a 20X magnification microscope for signs of neat biocide which has not been forced into the interstices of the resin particle.

The ingredients are present in the following wt. %:

| Ingredients | Example 12 | Comparative Example C |
|---|---|---|
| Polyvinyl Chloride resin (Diamond 450) | 62.0 | 87.0 |
| N—(2-methylnaphthyl) maleimide | 12.5 | 12.5 |

-continued

| Ingredients | | Example 12 | Comparative Example C |
|---|---|---|---|
| Dioctyl phthalate | | 25.0 | — |
| Calcium stearate | | 0.5 | 0.5 |
| | Total | 100.0 | 100.0 |

Substantial dusting during both discharge and blending is observed from the blend of Comparative Example C. Excessive biocide is seen on the particle surface and in the dry blend upon microscopic examination of the blend of Comparative Example C.

In contrast, no dusting during discharge or blending is observed from the blend of Example 12. Moreover, no biocide is seen on the surface of the resin particles nor in the dry blend.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A method of incorporating an effective amount of a microbiocide into a thermoplastic resin, said method comprising incorporating into said thermoplastic resin, in an amount which provides an effective concentration of the microbiocide in said thermoplastic resin, a microbiocide concentrate comprising a substantially non-dusting dry blend mixture of (a) a porous thermoplastic resin powder having a porosity of at least about 0.10 cc/g as measured by the mercury intrusion method or about 30% as measured on a void volume basis having a particle size between about 40 and about 300 mesh, and (b) a microbiocide, said microbiocide being present in the dry blend mixture at a concentration of at least about 20 times greater than the normal upper usage concentration of the microbiocide, and said microbiocide being within the pores of said thermoplastic resin powder, said porous thermoplastic resin powder being selected from the group consisting of polyvinyl chloride, polyethylene, polystyrene, polypropylene, nylon, styrene-butadiene copolymer, polycarbonate, polystyrene-polyphenylene oxide blend, polyphenylene oxide and ethylene/acrylic acid salt ionomer powders, and said microbiocide being selected from the group consisting of 10,10'-oxybisphenoxarsine; N-(trichloromethylthio)-4-cyclohexene-1,2-dicarboximide; 2,3,5-trichloro-4-propylsulfonyl pyridine; 2,3,4,5-tetrachloro-4-(methylsulfonyl) pyridine; zinc salt of 1-hydroxypyridine-2-thione; N-(trichloromethylthio) phthalimide; N-(2-methylnaphthyl) maleimide; cis-N-(1,1,2,2-tetrachlorethyl)-thio-4-cyclohexene-1,2-dicarboximide; 1-isopropyl-3-methyl pyrazolyl-5-dimethyl carbamate; 3-methyl pyrazolyl dimethylcarbamate; manganese ethylene bisdithiocarbamate; zinc ethylene bisdithiocarbamate; disodium ethylene bisdithiocarbamate; ferric dimethyl dithiocarbamate; zinc dimethyl dithiocarbamate; 2,4-dinitro-6-capryl phenol crotonate; p-chlorophenyl-p-chlorobenzene sulphonate; 2-N-octyl-4-isothiazolin-3-one; methyl-(butyl carbamoyl)-2-benzimidazole carbamate; 2-(4-thiazolyl) benzimidazole; copper 8-hydroxyl-quinolinate; α-diethoxyphosphinodithioacetylurea; α-dimethoxyphosphinodithioacetylurea; diethoxyphosphinodithioacetamide; dimethoxyphosphinodithioacetamide; bis(dimethylamido) phosphoryl flouride; 2-cyclohexyl-3-isothiazolone; 4,5-dichloro-2-cyclohexyl-3-isothiazolone and tributyl tin fluoride.

2. The method of claim 1 wherein the microbiocide is selected from the group consisting of 10,10'-oxybisphenoxarsine; N-(trichloromethylthio)-4-cyclohexene-1,2-dicarboxamide; 2,3,4,6-tetrachloro-4-(methylsulfonyl) pyridine; N-(trichloromethylthio) phthalimide; tributyl tin flouride; and N-(2-methylnaphthyl) maleimide.

3. The method of claim 1 wherein the thermoplastic resin powder is polyvinyl chloride and the microbiocide in N-(2-methylnaphthyl) maleimide or 10,10'-oxybisphenoxarsine.

4. The method of claim 1 wherein the amount of the dry blend mixture is between about 0.5 and 15 weight percent based on the total weight of the resultant composition.

* * * * *